United States Patent [19]
Klein et al.

[11] Patent Number: 5,987,352
[45] Date of Patent: Nov. 16, 1999

[54] MINIMALLY INVASIVE IMPLANTABLE DEVICE FOR MONITORING PHYSIOLOGIC EVENTS

[75] Inventors: George J. Klein, London, Canada; Dwight H. Warkentin, St. Paul, Minn.; Kenneth M. Riff, Plymouth, Minn.; Brian B. Lee, Golden Valley, Minn.; James K. Carney, Eden Prarie, Minn.; Gregg Turi, Budd Lake; Anthony J. Varrichio, Flanders, both of N.J.

[73] Assignee: Medtronic, Inc., Minneapolis, Minn.

[21] Appl. No.: 09/033,678

[22] Filed: Mar. 3, 1998

Related U.S. Application Data

[63] Continuation-in-part of application No. 08/678,219, Jul. 11, 1996, abandoned.

[51] Int. Cl.⁶ .................................................. A61B 5/0402
[52] U.S. Cl. ........................................................... 600/509
[58] Field of Search ............................... 600/509; 607/36

[56] References Cited

U.S. PATENT DOCUMENTS

| | | |
|---|---|---|
| 4,223,678 | 9/1980 | Langer . |
| 4,407,288 | 10/1983 | Langer . |
| 4,556,063 | 12/1985 | Thompson . |
| 4,825,874 | 5/1989 | Uhlemann .............................. 600/509 |
| 4,844,090 | 7/1989 | Sekine ................................... 600/509 |
| 5,111,396 | 5/1992 | Mills . |
| 5,226,425 | 7/1993 | Righter . |
| 5,289,824 | 3/1994 | Mills . |
| 5,313,953 | 5/1994 | Yomtov . |
| 5,333,616 | 8/1994 | Mills . |
| 5,365,935 | 11/1994 | Richter . |
| 5,370,663 | 12/1994 | Lin ............................................ 607/36 |
| 5,404,887 | 4/1995 | Prather . |
| 5,411,031 | 5/1995 | Yomtov . |
| 5,417,717 | 5/1995 | Salo . |
| 5,464,431 | 11/1995 | Adams . |
| 5,464,434 | 11/1995 | Alt . |
| 5,511,553 | 4/1996 | Segalowitz . |
| 5,513,645 | 5/1996 | Jacobson . |
| 5,518,001 | 5/1996 | Snell ...................................... 128/697 |

OTHER PUBLICATIONS

Krahn, Andrew, "The Etiology of Syncope in Patients with Negative Tilt Table and Electrophysiological Testing", *Circulation*, p. 1820, 1995.

Leitch et al., "Feasibility of an Implantable Arrhythmia Monitor", *PACE*, vol. 15, Dec. 1992 p. 2232.

*Primary Examiner*—Scott M. Getzow
*Attorney, Agent, or Firm*—Harold R. Patton; Michael B. Atlass

[57] ABSTRACT

A minimally invasive implant, means for insertion, and description of how to most efficiently use it are described n several embodiments. This implant preferably has a segmented looping memory for storing triggered physiologic events. Preferred events for setting autotriggers to record physiologic signals occurring during events include arrhythmias and syncopal events. Preferably the device can function without a microprocessor. An outside device or other patient activated manual trigger is included. Auto triggers and manually set triggers may be of different sizes. The preferred physiologic events are ECG signals. Electrode spacing can be critical. Additional sensors may be provided to the device. Preferred communications with the device is through telemetry such as is used for pacemakers and other implanted devices.

22 Claims, 13 Drawing Sheets

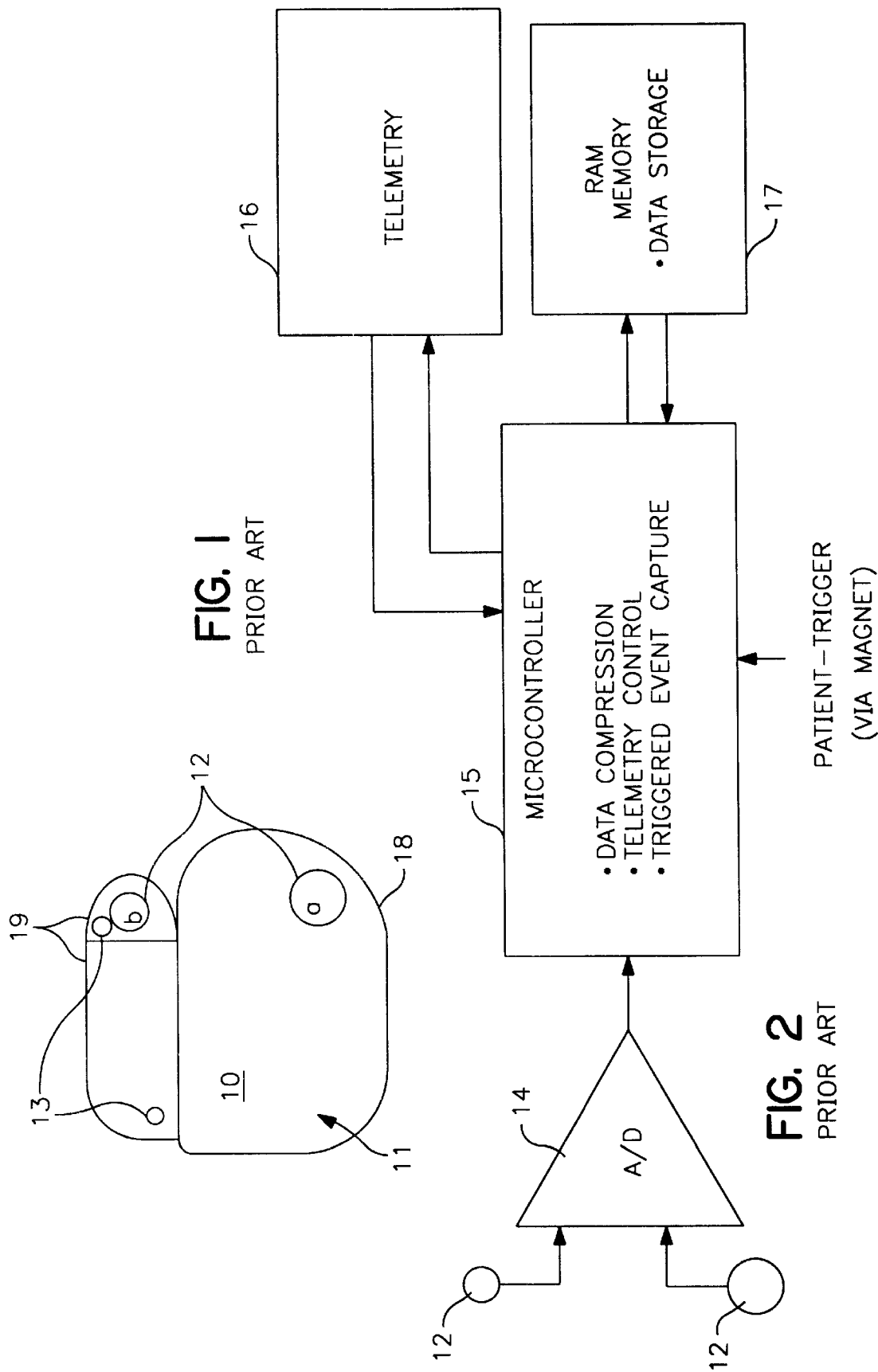

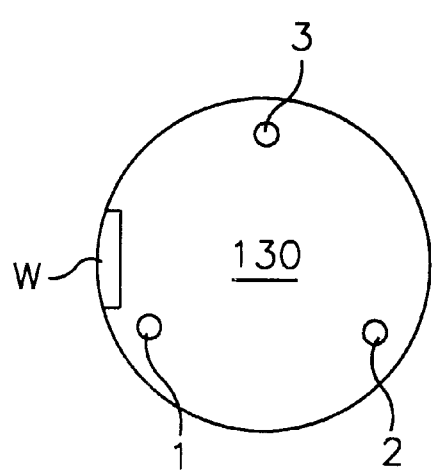
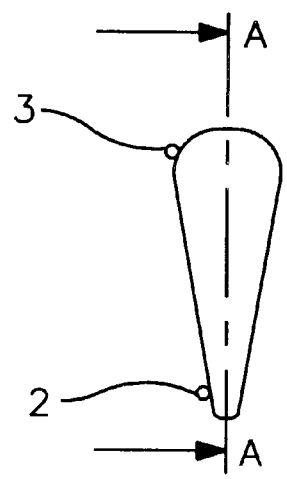
FIG. 13A                FIG. 13B
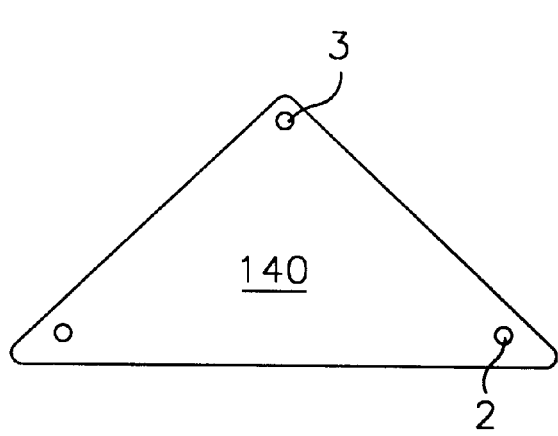
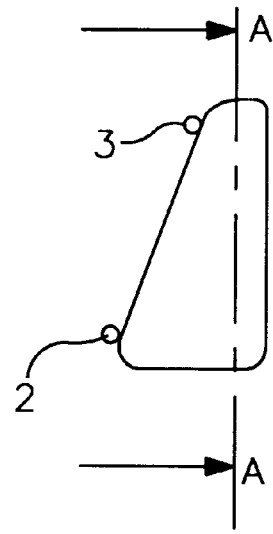
FIG. 14A                FIG. 14B

MINIMALLY INVASIVE IMPLANTABLE DEVICE FOR MONITORING PHYSIOLOGIC EVENTS

This application is a CIP of Ser. No. 08/678,219, filed Jul. 11, 1996, now abandoned.

This invention relates to an implantable monitoring device for sensing physiologic events with minimally invasive intrusion into an animal or patient body, and is particularly well suited for long term monitoring of body events like ElectroCardioGrams (ECG's) and in monitoring other body physiologic events related to heart function which may include for example, but not by way of limitation, such parameters as temperature and tissue oxygen levels relevant to normal and abnormal cardiovascular function. By enabling easy monitoring and recording of physiologic events in the patient's body, such events can then be studied at leisure outside the body, providing research, diagnostic and therapeutic opportunities not otherwise available.

BACKGROUND OF THE INVENTION

Syncopal events and arrhythmias of the heart are particularly problematic for diagnostic physicians to observe in living patients. These events, can be of short duration and sudden onset, coming with little or no warning, and may happen very infrequently. Holter monitors are well known for monitoring electrocardiograms periods of time amounting to days or perhaps a week, but these are bulky and are applied externally to the body and interfere with the patient's normal life, making them impractical for long term use. Further, patient compliance cannot always be guaranteed, and is a common problem in use of the Holter devices. Problems with external monitors and associated recorders also include inability of some patients to abide the attendant skin irritation. Bulky or expensive special purpose devices may need to be available and maintained. Removal is required for showering, and so on. Any time a living body needs to have a long term monitoring of a physiologic event that is intermittent or infrequent or both, all these problems come into focus. Therefore, there exists a need for minimally intrusive long-term monitoring of the patient's physiologic events and status. This is particularly indicated in, but not limited to patients with cardiac arrhythmias and vasovagal syncope to provide sufficient evidence for diagnostic purposes and for research into the causes and effects of such events. Patients have come to accept long term implants of small items for many things, including birth control, for example, like the "Norplant" (™ of Wyeth Laboratories) devices which secrete birth control hormones for perhaps a year before they need replacing. Accordingly it is believed that small device implants for long term implant will be well tolerated by the patient population to be served by this invention.

Many attempts to address some of these problems have been made and met with limited success. The problem has been long existing. The Instromedics approach is seen in the Mills, et al patents (U.S. Pat. Nos. 5,333,616; 5,289,824 and 5,111,396) for a wrist worn monitor for ECG's which include features like patient triggering and microprocessor determination of event types (QRS detection). Wrist worn devices are also shown in the Righter patents issued to assignee Ralin, including U.S. Pat. Nos. 5,226,425 and 5,365,935. Jacobsen, et al in U.S. Pat. No. 5,513,645 describes multiple resolution storage for ECG's (ELA Medical is the assignee), and Snell's U.S. Pat. No. 5,518,001 vaguely describes a patient triggered recording device with multiple sensors and patient triggering(assigned to Pacesetter). InControl's approach is seen in the Yomatov patents, U.S. Pat. Nos. 5,411,031 and 5,313,953 which seems to concentrate on beat to beat timng records, suggests the use of an arrhythmia detector, and does mention the possibility of leadless electrodes for monitoring cardiac signals. Examples of an external monitor/recorders can be found in Segalowitz' patents, including U.S. Pat. No. 5,511,553, and Salo's U.S. Pat. No. 5,417,717. Another well known event recorder is the "King of Hearts" (™ of Instramedix) which records pre-event and post-event data.

Monitoring can be done using implantable pulse generators such as pacemakers and other heart stimulating devices or devices with leads in the heart for capturing physiologic parameters, including the ECG. However, the expense and risk from implanting an intracardiac lead and/or a pacemaker with special monitoring functions is something both patients and physicians would prefer to avoid. Such devices, in addition to performing therapeutic operations, may monitor and transmit cardiac electrical signals (e.g., intracardiac electrograms) to an external diagnostic devices typically with leads fixed in the patient's heart, to observe electrical activity of a heart. It is common for implanted cardiac stimulation devices to send intracardiac electrogram signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

For example, U.S. Pat. No. 4,223,678, entitled "Arrhythmia Recorder for Use with an Implantable Defibrillator", issued to Langer et al. on Sep. 23, 1980, discloses an arrhythmia record/playback component within an implantable defibrillator. ECG data is converted from analog to digital (A/D) form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry. Langer et al. in U.S. Pat. No. 4,407,288, entitled "Implantable Heart Stimulator and Stimulation Method", issued Oct. 4, 1983, discloses a programmable, microprocessor based implantable defibrillator which senses and loads ECG data into a memory via a direct memory access operation. A processor analyzes this ECG data in the memory to detect the occurrence of an arrhythmia event afflicting a patient's heart. Upon such an event, the defibrillator may generate a therapy to terminate the arrhythmia event and store the ECG data sequence of the event, for transmission to an external monitoring device and later study. In normal circumstances, when no arrhythmia event is occurring, the defibrillator continuously overwrites the ECG data in the memory.

U.S. Pat. No. 4,556,063, entitled "Telemetry System for a Medical Device", granted to D. L. Thompson et al, 1985, teaches a pulse interval telemetry system capable of transmitting analog data, such as sensed intracardiac electrogram signals, without converting analog data to a digital numeric value. The Thompson et al. telemetry system is capable of sequentially transmitting both digital and analog data, individually and serially, in either an analog or a digital format, to a remote receiver. The features and capabilities of these pacemaker/defibrillator devices is now well known, but the problems in long term monitoring for events and adequate recordation remain.

In the December 1992 Vol. 15 edition of PACE (15:588), a feasibility study was done for implantable arrhythmia monitors and reported in an article by Leitch et al. Subcutaneous, Bipolar "Pseudo-ECG" Recordings using an Implantable Monitoring System and at chaired poster presentation of the North American Society of Pacing and Electrophysiology (NASPE) an implantable monitoring system was described using the pacemaker that had been altered to use a point on the can as an electrode and to have an electrode mounted into the connector block thereof. This was presented to NASPE in Munich in 1994 by Brian Lee of Medtronic, Inc. A photograph of the device shown in that poster presentation was published by the American Heart Association Inc. in 1995 by Andrew Krahn, M.D. in an article entitled "The Etiology of Syncope in Patients with Negative Tilt Table and Electrophysiological Testing", pp. 1820 of CIRCULATION, 1995; 1992. The initial thinking for this started in NASPE 1991 in an Abstract published in PACE, 1991, 14:677 authored and titled: Leitch, J W, Klein, G J, Yee, Lee B B, Kallok, M, Combs, B, Bennett, T: Feasibility of an Implantable arrhythmia Monitor.

Further, a leadless implantable sensor for cardiac emergency warning was described in U.S. Pat. No. 5,404,887 issued to Knowlan et al. which detects heart events through impedance measurement sensed using a coil. See also Yomato et al, U.S. Pat. No. 5,313,953 which describes (in FIG. 26) a large but leadless implant.

With sufficient hardware and connections to the body, numerous other physiologic parameters may be sensed as is pointed out in U.S. Pat. No. 5,464,434 issued to Alt and U.S. Pat. No. 5,464,431 issued to Adams et al.

Accordingly, there still exists a need for a more acceptable recording and monitoring device capable to maintain a data record over a long period of time and highlighting or least capturing those physiologic events that are of interest to a diagnostic, research or therapeutic study, and particularly those physiologic events that are required for correct diagnosis and therapy. Further, it has heretofore been unreasonably expensive and overly invasive to the patient to implant monitors for simple recording functions and particularly to implant intracardiac and intravascular monitors for simple recording functions. Many of the features of this invention are designed to ameliorate both these problems.

BRIEF DESCRIPTION OF THE DRAWINGS

FIGS. 1 and 2 are the exterior side view, interior block diagram, respectively of a prior art device.

FIGS. 13a, 13b, 14a and 14b are front and side views of alternate embodiments of the invention.

SUMMARY OF THE INVENTION

Figure 3:
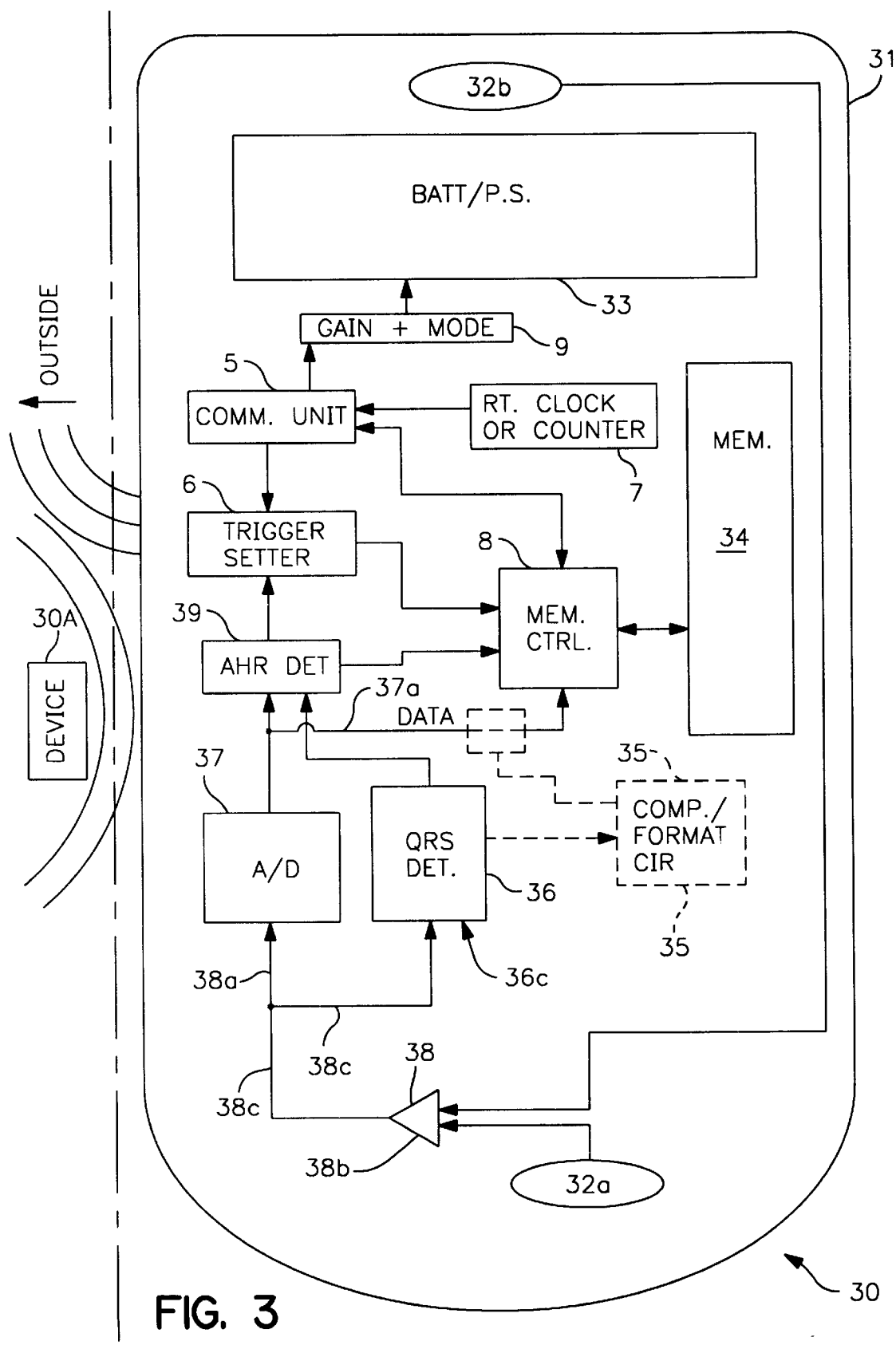
FIG. 3 is a block diagram illustrating the main circuit and assembly of a device in accord with a preferred embodiment.

Objects of this invention include providing a minimally intrusive implantable system capable of communicating with an external device and having electrodes separated by a fixed distance to measure a subcutaneous electrogram including a signal input means, here shown as an amplifier, a looping memory, and a circuit for controlling the memory, the device having an external configuration and dimensions maximally adapted to such needs.

Numerous features are included to facilitate the implantation, management, and orientation in the body of the implanted device. A preferred data compression scheme is also disclosed as is automatic selection of time periods pre and post triggering.

In its presently most preferred embodiment it provides for long term ECG monitoring. It has the capacity to use manual or automatic triggers or both to cause the memory to store events in reserved areas of a looping memory, preferably in identifiable memory partitions. It can accept limited programming or mode control and can read out sections of or all of the memory when prompted from the outside by a physician or other user, provided they have the appropriate external device to initiate and receive such transmissions from the implanted inventive device.

DETAILED DESCRIPTION OF THE PREFERRED EMBODIMENT

Prior to this invention the only consistent use of implantable electrode sensing systems employed leads located in the heart because of the quality of the signal obtained that way. Subcutaneous electrodes (below the skin) have not been demonstrated to be highly effective in producing good monitoring devices, and have not found commercial medical success. A well known example of a system having leads which also contained more than a single electrical contact in the body of the pacemaker was described in U.S. Pat. No. 5,331,966 issued to Bennett et al. in 1994. In column 8 of that patent, several other implantable recording systems are described. The data recording system described in this invention requires only two electrode surfaces.

The closest prior art is described with reference to FIG. 1 and appeared at a NASPE (North American Society of Pacing and Electrophysiology) conference as a poster presentation in 1994. The device 10 was provided with two suture holes 13 and two spaced apart non-lead or leadless electrodes 12 at one and one-quarter inches distance center to center. The device was coated with paralene indicated by arrow 11 so that the only area of exposure on the body of the pacer can 19 is the exposed area at the electrode 12a. The other electrode is a metal plug electrode 12b mounted in a connector block 19.

In FIG. 2 the same electrodes 12 supplied signals into the circuitry inside the housing or "can" 18 (FIG. 1) by first entering a analog to digital conversion and amplifier circuit 14. Data from this circuit 14 was fed to a microcontroller 15 which provided functions of data compression, telemetry control and event capture triggered by patient operation. Telemetry block 16 and RAM memory storage 17 were also provided in this device. The device described in the Yamato et al patent, (U.S. Pat. No. 5,313,953, FIG. 26) is quite complex and in any case, built for deeper implant than is this invention in its preferred uses.

Practical considerations in adopting preferred structure design

A small and easy-to-implant, primarily leadless device or one having a very short lead-like structure, device will require a minimal incision size, which is good for the patient. This can vary if the physician wants to use sutures to hold the device in place or for other reasons as needed. Between ½ and 1 inch incisions are preferred to avoid trauma and scarring. If significant concern exists regarding scarring, both ends can be tapered.

For ease of insertion the device should be easy to self-position, and preferably elongate in shape to maximize signal strength for a given volume by having electrodes spaced at far ends of the length or longitudinal axis of the device. The larger the device the more electronics and larger the battery volume can be. Both the functionality provided by extra electronic circuits and battery volume may be traded for enhanced useful life and minimal complexity when considering the optimum device size. Although it is preferred that the electrodes be widely spaced on opposite ends of an elongate device, variations to this theme may be acceptable for alternative monitoring missions. The primary mission of the preferred implant is long term ECG event monitoring.

Refer now to FIG. 3 in which a circuit model 30 is illustrated in an outline of an implantable device shell 31. Electrodes 32a and 32b bring signal from the body to an input mechanism 38, here drawn as a differential amplifier for simplicity only, the output of which is fed to a QRS detector 36 and an A/D converter 37. Both these circuits 36 and 37 supply output to an arrhythmia detector 39, which in this preferred embodiment supplies the autotrigger signal to the trigger setting circuit 6. The data output from the analog to Digital converter may be converted, compressed, formatted and marked or reformulated if desired in a circuit 35 before the data is ready for input into the memory 34. The Memory control circuits 8 receives input from the A/D converter, with or without conversion and so forth from circuit 35, from the auto triggering determination circuit (here seen as the arrhythmia detection circuit) 39 (which may include input directly from the QRS detector if desired) as well as signals from the trigger setter circuit 6. The trigger setter circuit may also be controlled by a communications unit 5 which operates to receive and decode signals from the outside of the implant 30 that are telemetered or otherwise communicated in by a user. This communications unit 5 will also be able to communicate with the memory controller to request the offloading of memory data for analysis by an outside device. It should contain an antenna a or other transceiver device or circuitry to communicate with an outside device such as device 30A. A clock or counter circuit 7 reports the time since start or real time to the outside interrogator device 30A contemporaneously with a data offloading session so that the events recorded in memory 34 may be temporally pinpointed.

Alternatives to this overall design may be considered, for example by using a microprocessor to accomplish some or all of the functions of circuits 6,8, 39, and 35 but it is believed that such a design will not provide the power and size savings taught by use of the preferred design.

Figures 4A, 4B, 4C:
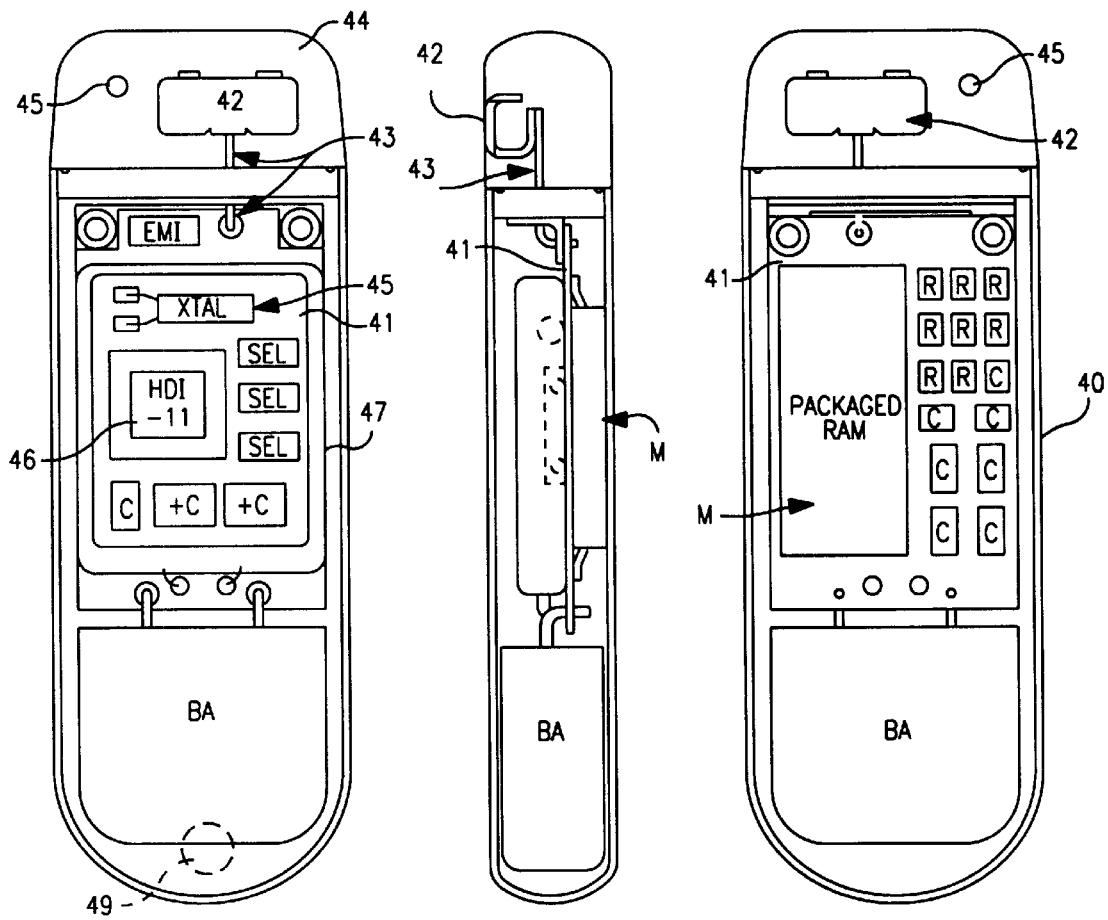
FIGS. 4a, 4b, and 4c are exposed front, side, and back views, respectively of a preferred embodiment of the invention.

FIGS. 4a–c illustrate one preferred form 4 of the invention. In this form it has an outer titanium shell 40, in a plastic cap means 44, which together form the exterior of the device. The cap means 44 may be composed of material similar to those used for pacemaker connector blocks as it is in the is case. The two electrodes, 44 and 49, provide metal surface contacts to the body. Electrode 49 is formed as a whole in a paralene coating over the metal body 40, of the device. The metal electrode 42 is connected via a feedthrough 43 which is itself electrically connected to the circuit board 41. Circuit board 41 contains all the electronics required for the device function and is connected to a battery BA for power. An integrated circuit 46 houses circuitry and intelligence required for the function and the memory M is packaged on the other side of the circuit board. In this preferred form, the invention uses a communications circuit 45 having a telemetry antenna both to indicate from outside the body that a read out is requested of the device, and for communicating data out from said device. Programming of the device or mode setting will also use the communications circuit 45. In this form also a suture hole 45 is provided through the cap means 44. Electrode 49 is connected by a conductive connection (not shown in this fig.) to the circuit board. In this embodiment the length "l" is 2⅜" and "w" is ¾". These measurements can be varied within the constraints described. Electrode spacing here is about 1¾", center to center.

Presently less preferred three or more electrode embodiments are also described with reference to FIGS. 5–8. A third electrode, like electrode 56, can be used to optimize signal strength responsive to changes in device position, heart position, or body position. A transistor or other switch means can switch the electrode configuration automatically based on a determination of signal strength or direction from an outside device through the communications circuit. In order to retain the elongated shape yet provide a well spaced orthogonal position, the third electrode can be mounted on a self-positioning (flexible, rigid, or semi-rigid) stubby lead. An additional variation from the most preferred design could provide for a wing or fin-shaped member 57 or more than one wing (57, 56) that extend substantially in one plane from the main body of the device. Ideally this would be approximately in the same plane as the other two electrodes (53 and 59). Unless they are constructed so as to spring from the main body outward after insertion into the intended body area, wings like 57 or 58 will require a larger incision than the currently most preferred device, a smooth bodied device. The illustration of the device 50 in FIG. 5 without the dotted line external parts 55, 57, 58, and 60, would be such a most preferred form.

Some other features are also significant and should be noted. A single suture hole 54 (or two or more if desired) can be provided in the cap. Additional suture appendages, like ring 60, having a suture hole 60a, may additionally be provided for more stability. Additionally, a suture may secure the stubby lead to the patient's tissue if desired. These suture holding means allow the device to be fixedly held in one orientation in the body of the user, whether intramuscular or strictly subcutaneous. Intramuscular pocket implantation is advantageous in that the device may be protected form the outside world by a layer of muscle, which will provide cosmetic benefits to the patient as well. The exact sites of implant may advantageously be varied from patient to patient for various reasons apparent to the physician. Implant just under the skin now appears to provide the signal most free of skeletal muscle myopotential or body movement signal interference.

Figure 15:
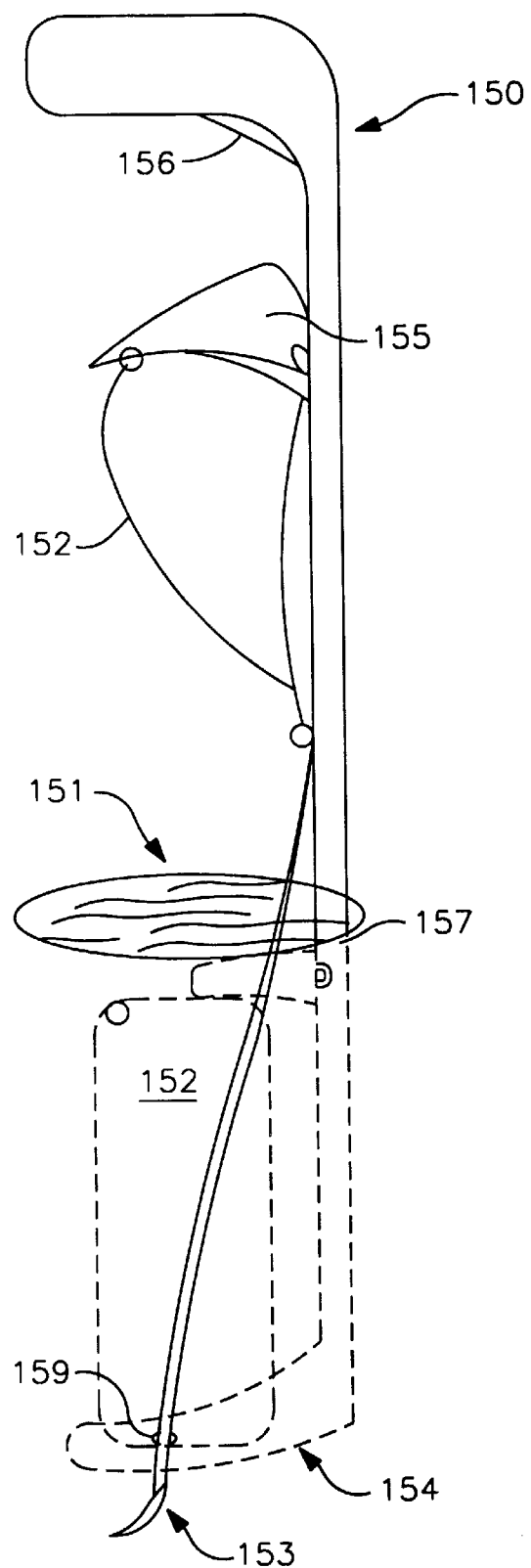
FIG. 15 is a rough sketch of an insertion tool for implanting the device in accord with this invention.

Another important feature of the shape is to have one end of the elongated device tapered to aid in easily inserting under the skin during implant/insertion (as in a blunt dissection procedure). This self-placing tapered tip helps ensure that the device stays positioned properly in alignment with the principal cardiac vectors whether they be the principal R-wave, or P-wave vector or best for both, especially where two sutures would be used at the cap end. It is believed that this taper feature will be better than just a blunt placement with an instrument. Another preferred method of implant could be injection of the tapered end into the body, using a device similar to that described in the U.S. Pat. No. 5,520,660, the Implant Plunger. As a secondary feature the other end from the insertion tip may be blunt or otherwise formed to assist in providing a better directing and pushing surface during insertion. A rough sketch of an alternate tool is provided in FIG. 15, in which a handle unit with a blade 154 makes an insertion into the opening 151 created in the skin, holding the implant 152 between a recess behind the blade and a pushing member 157 until a handle releases the pushing member. The handle 155 may advantageously tie the end of a suture into the patient beneath the skin with tool 153, which is then retrieved by manipulation of a wire 157, thus accomplishing insertion and securing the implant at the far end 159, rather than at the cap end of the implant. Many variations on this injection and insertion theme can be accommodated within the teachings of this document.

These kinds of instrument assisted insertion are herein referred to generally as insertion via a "trocar" concept. In general this "trocar" concept involves any instrument which encloses the implantable device and contacts the surface of the body or point of incision, starts the incision and allows the device to be inserted thereinto. The trocar is used to make a starting hole/incision using a sharp point and/or cutting edge first. The physician then uses the mechanical advantage provided by the trocar to stretch the incision wide enough to allow the implantable device to fit through the incision and then pushes the device under the skin (or into the muscle, etc.) in one motion. The incision could be enlarged to facilitate suturing if desired.

A preferred form of insertion tool should be fitted with a smooth protective chamber (preferably plastic lined) just wider than the implantable device (but of approximately the same cross-section) to slip the implantable device into, tapered end toward the insertion end of the tool. The bottom of the chamber could be shaped to fit the taper of the implantable device and would move out of the way when the implantable device was pushed by hand or an injecting plunger. The outside of the bottom of the chamber would come to a sharp point and possibly have cutting edges tapered back on both sides from the sharp point, but may not need to cut to the full width, instead it could stretch the initial opening to allow insertion of the implantable device with a push.

Suturing to hold the implant device in place could be done automatically or with surgical staples by some means associated with the tool, the device could be left in the pocket, or it could be held in place by a coating of its surface with a sticky substance or one that adheres to body tissue like silicone rubber, or it could be inserted with a properly shaped Parsonnett pocket, although this would likely interfere with the gathering of signal through the electrodes.

Figure 5:
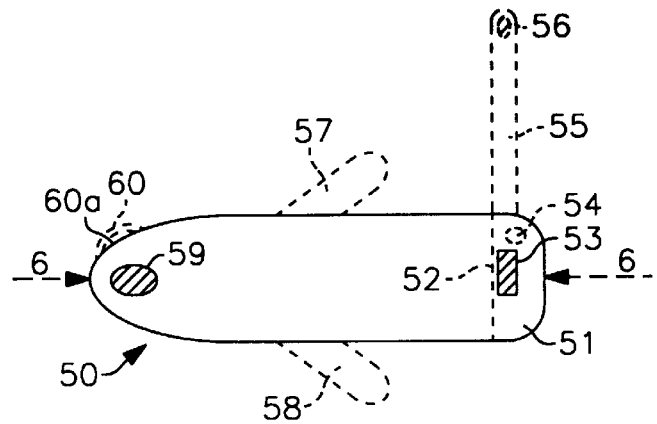
FIG. 5 is an illustration of a preferred embodiment of the invention, showing (in dotted line), locations for fin/wing and stubby lead features.

While considering the features of the embodiments illustrated by FIG. 5, it is well to note the electrode configuration. Here the electrode 53 is a conductive or metal plate compatible with the patient's body that is on one surface of the cap unit 51, the cap being delineated by dotted line 52. One can construct the device 50 as a solid container having out of body compatible materials. For examples, titanium or other metal or alloy, coated with compatible insulator but exposed for at electrode areas or fitted with conductive electrodes, ceramic having conductive areas thereon, etc. One should have two surface electrode areas separated by a distance (functionally similar, therefore, to electrodes 53 and 59 in FIG. 5) for the device to work. This distance should be at least far enough to achieve good signal but not too far so as to make the size of the implant too large to accommodate. The first devices had electrode separation distances of just over 1¾" center to center and we currently believe the best separation distance to be approximately that. This distance can range between ½ and 2½ inches, or even near 4" before becoming impractical.

Figure 6A:
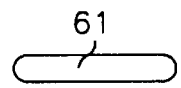
FIGS. 6a and 6b are front and side views of preferred embodiment cross-sections taken from FIG. 5.
Figure 6B:

In the presently preferred embodiment the cross-section is an easy-to-insert rounded rectangular or oval shape to the potential of the device turning over after implant. FIG. 6A shape 61 and FIG. 6B, shape 62 illustrate this concept and the reader may use any similarly functional cross-sections. Our studies have determined that electrodes which are faced outward, toward the skin of the patient, are preferable to face in or other electrode orientations. This may be due to less muscle exposure or movement or other noise sources.

Figure 7A:
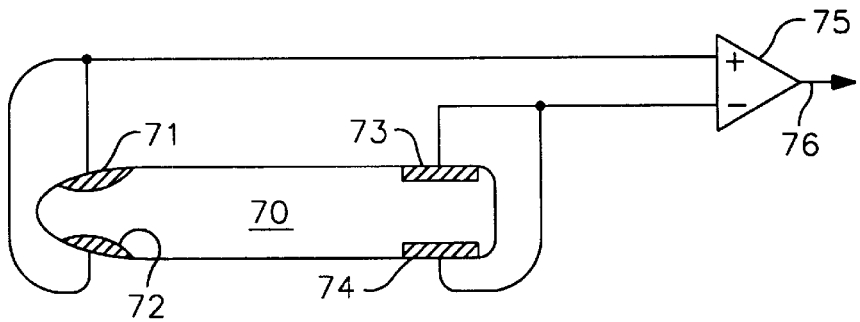
FIGS. 7A, and 7B are front, and cross section views of another preferred embodiment of the invention.
Figure 7B:
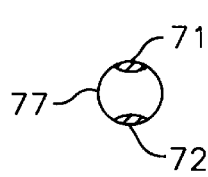

Additional features are illustrated which can assist in preventing medically unintended movement of the device. In FIG. 7A the electrodes are placed so as to be matched on opposite sides of the rectangular, round, or ovoid shaped device and electrically connected in parallel on opposite sides to retain the same signal in spite of flipping or other movement. (The internal circuitry would operate like the op-amp 75 to produce output 76 from electrodes 71–74 as shown to produce this effect.) In surface pacemaker implants, patient populations have been known to play with their implants, often unconsciously and this has been a common enough problem in the pacemaker art to have obtained the name "twiddler's syndrome." These features address this problem. The device of 7A is seen in cross-section in FIG. 7B.

Figure 8:
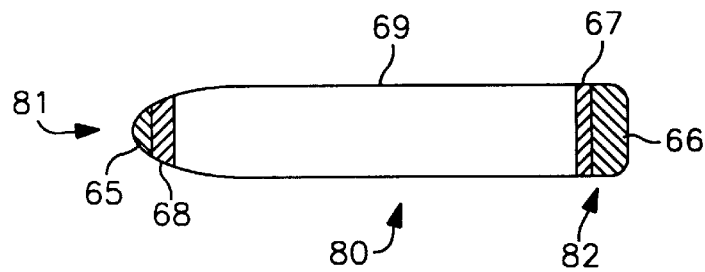
FIG. 8 is a front view of another embodiment of the invention.

Another feature in a preferred embodiment employs circumferential electrodes on a cylindrically shaped device. In FIG. 8 this device can be seen to also have a body 69 that is tapered on one end 81 and blunt on the other 82. The effect again is to provide a constant signal in spite of likely unwanted rotation of the device, because the electrodes each extend around the device circumference. Here the electrode area positions are illustrated for each end, 65 and 68 for end 81 and positions 66, 67 for end 82. This approach trades-off the protection from muscle noise of the rectangular outward-facing device.

Additional designs for the device shape which would be employed if the circuitry and power needs could be reduced in size are shown in FIGS. 13a, device 130 and 14a, device 140 with side views in the corresponding FIGS. 13 and 14b. These devices have three electrodes each, 1, 2, and 3, to adjust orientation to the best signal if desired, however two electrode forms and forms with windows W for sensors are also contemplated.

Procedure for Non-Invasively Determining Optimal Implant Position and Orientation Prior to the Implant One of the preferred ways to use the invention is to be careful to assure that the device is implanted in substantially the optimal position and orientation. For obtaining the best ECG signals with a two electrode device this is especially important. A simple and noninvasive determination of the proper position and orientation prior to implant can be made by merely employing an external ECG measurement device using external electrodes (of any of a number of standard types well known in the field of cardiology). By observing the ECG at orthogonal electrode orientations in roughly the positions preferred by the physician/patient, the signal amplitudes both P and R wave can be monitored until a good positioning is found and the signals are optimal. It is preferred that these measurements be made in several typical patient postures to account for posture variability as well.

The electrodes should be approximately spaced with the same spacing (within a factor of two or so) as the implantable device and with approximately the same diameter electrodes as the implantable device (a factor of two or so as well). (The diameter of the external electrodes in most ECG systems will be smaller than the edge to edge spacing of the electrodes by greater than roughly a factor of two or so). We outline two approaches here.

Approach 1

Figure 9:
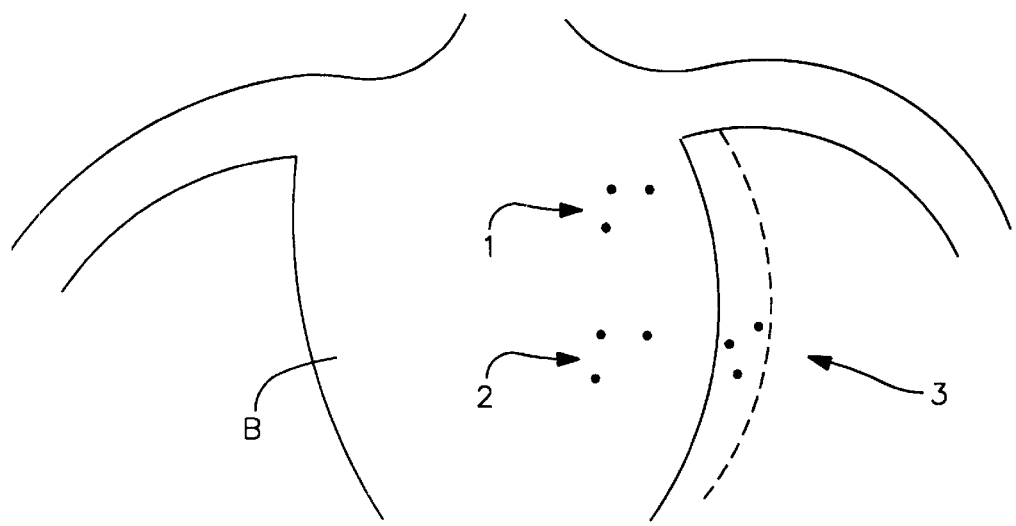
FIG. 9 is a drawing of a patient body segment with specific locations referenced thereon.

Standard ECG Electrodes: a standard ECG Monitoring System can be used with the standard electrodes and electrode preparation of the skin. The electrodes are then placed in orthogonal patterns of the proper electrode spacing over each candidate implant site (as described in the above paragraph) per FIG. 9.

Orthogonal measurements over each candidate implant site (here illustrated as 1, 2, or 3, for example locations for three electrodes each though two could be used) can be used to determine the optimal orientation.

One can either simply look at the signal amplitudes using the orthogonal electrodes and assume a similar implant orientation will be substantially as "good." One may try again until a satisfactory signal at a given location and orientation is obtained For a more exact orientation to produce the absolutely best and largest R-wave one can do simple vector arithmetic in the following manner:

If the two orthogonally oriented electrode pairs with a common electrode produce R-wave Amplitudes A and B, the optimal orientation will be at the angle=Arc-Tangent(B/A), where this angle is taken from the common electrode to the electrode producing R-wave amplitude A. The same procedure can be followed for optimizing the P-wave amplitude. One can also use similar calculations to determine the best compromise angle for P and R waves.

This Standard ECG approach has the advantage of being possible using commonly found ECG Monitoring systems, but has the disadvantage of requiring surface preparation of the skin, as well as additional calculations or repeated tries if the "best" orientation is desired.

Approach 2

Figure 10A:
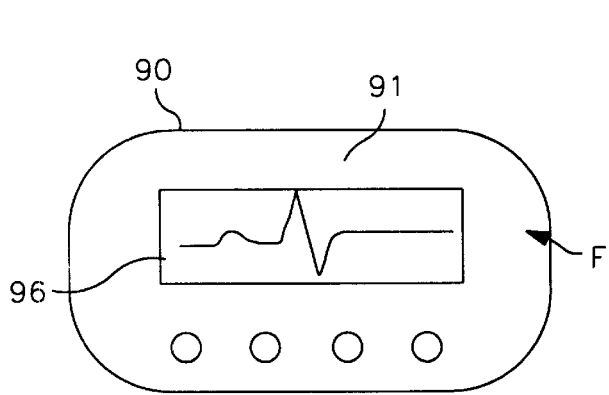
FIGS. 10A and 10B are front and back views of a testing ECG device for use with this invention.
Figure 10B:
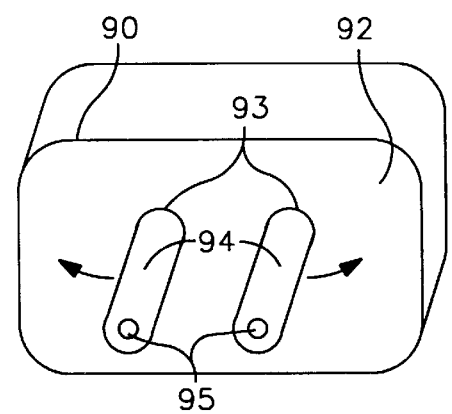

Hand-Held Device with Fixed Electrode Probes: In this approach a special device similar to hand-held emergency heart monitors provided by several manufacturers can be used to probe the surface locations and orthogonal orientations that are desired in order to find the optimum orientation. This device needs to be customized to have electrode probes which are roughly the same spacing as the implantable device and looks like FIG. 10A. The ECG is either displayed on an attached recording device or display or on a built-in display such as an LCD monitor. The procedure can also use a customized hand-held portable ECG monitor with only slight modifications to produce a satisfactory result. For example the Micromedical Industries Inc. (Northbrook, Ill.) Paceview(tm) with the modification shown in FIG. 10B could be used. It has a raised electrode assembly constructed on points 93 which support posts 94 and electrodes 95, configured so as to maintain the proper test position of the electrodes for the device being considered for implantation. This added structure is on back side 92. Because these additional structures have a spacing similar to that of the implantable device, the readout on side 91 will produce fine results for placement and orientation data.

This device 90 has the advantage of not requiring the placement of surface electrodes over the implant site, is fast enough to allow a simple sequential test at each orientation and implant site, and has no wiring or external equipment required. The ECG can be seen in real time in monitor window 96.

Functional considerations for the preferred embodiments

In FIG. 3 the inventive system is described as stated above. The external device 30A is preferably a device that is commonly called a "programmer" in the pacemaker art, because it's usual function is to communicate with and program implanted devices. Software modifications and modifications to the telemetry system of device 30A to accommodate communication with and analysis of data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for mere ECG monitoring and event triggering is minimal, so in the preferred embodiments that only monitor some form of ECG or other limited sensory input, a microprocessor can be and is done away with altogether by using particularized functional circuits instead of doing the functions in software.

Figure 3A:
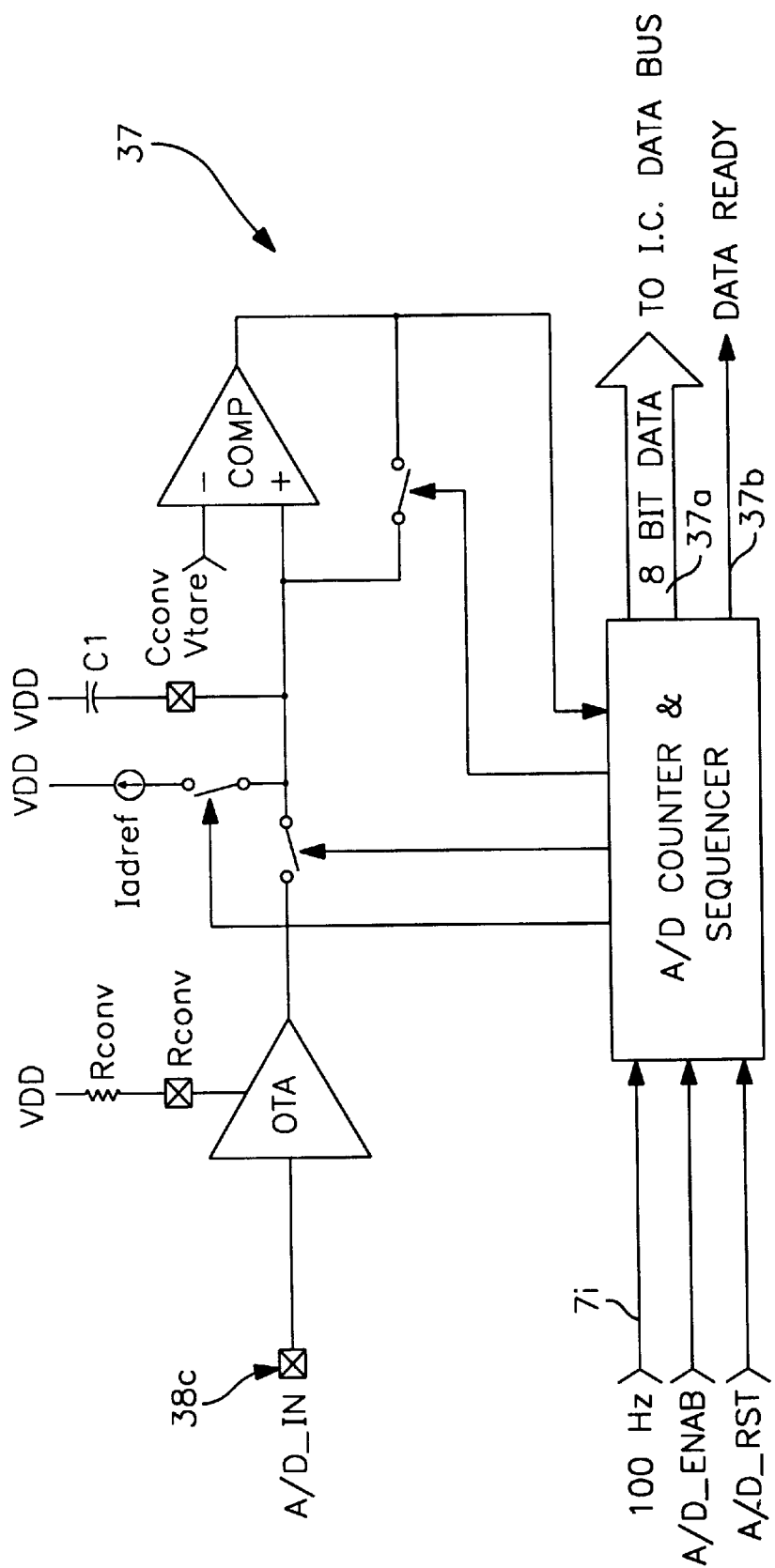
FIGS. 3A–D are block diagrams of preferred embodiment circuits of the implanted device used for monitoring and storing ECGs.

In FIG. 3A, a block diagram of an analog to digital conversion circuit for use in this invention is shown. The clock input may advantageously use an output from the clock circuit 7, input 7i. The input 38c is the analog input signal from input circuit 38, and the converted output is a stream of 8 bit digital data words on line 37a, sequenced by a timing line 37b.

Figure 3B:
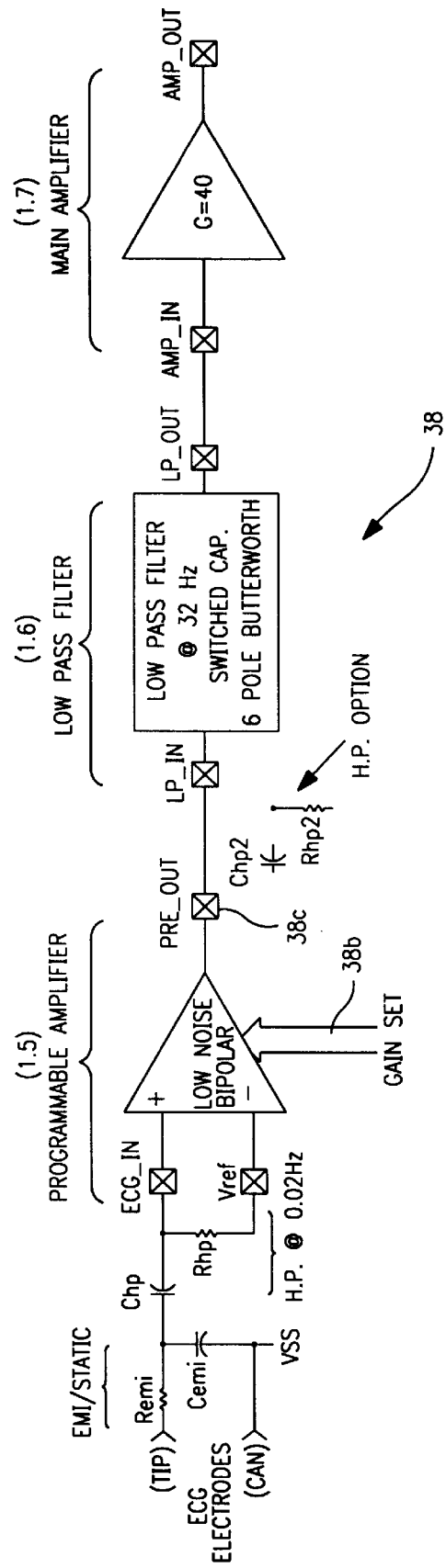

FIG. 3B illustrates the basic parts of circuit 38, additionally indicating the input of gain set bits which can modify the value of the output of the low noise bipolar amplifier for output at line 38c, the input to the QRS detector. In this invention QRS detection is done on the analog signal, advantageously saving more complex detection after digital conversion.

Figure 3C:
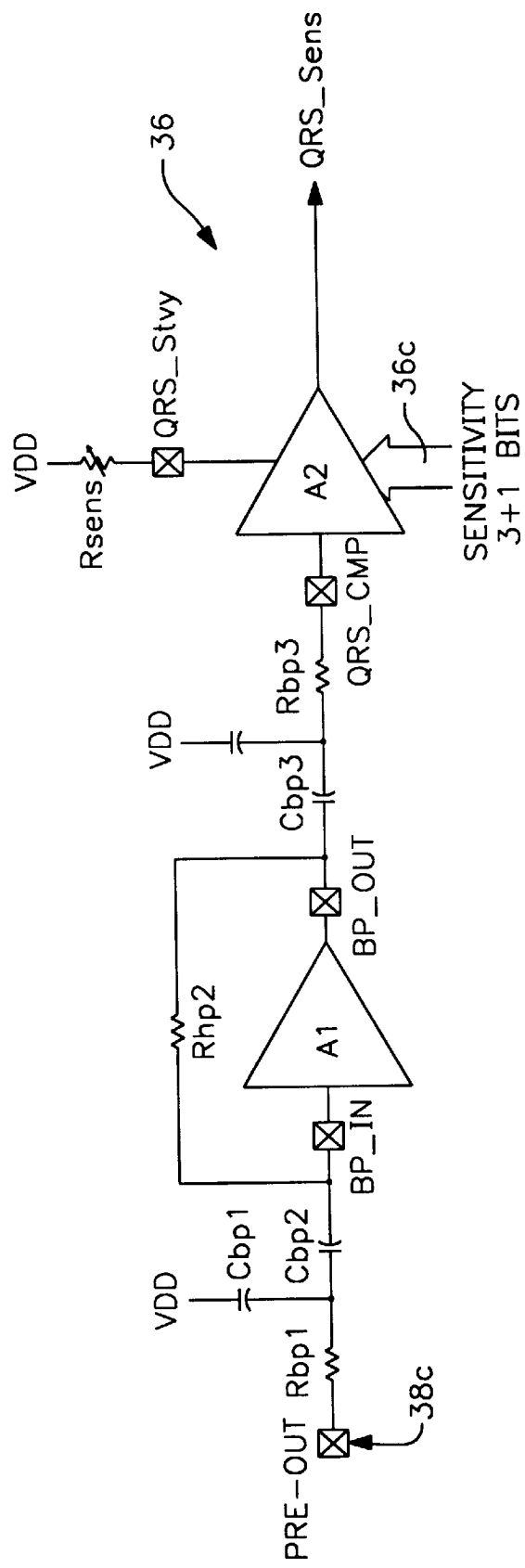

In FIG. 3C QRS detect circuit 36 has a 2nd order bandpass filter with a center frequency preferably in the 20–25 Hz range. It includes a transconductance amp A1, summing amp/comparitor A2 and resistors Rbp1-3, capacitors Cbp1-4 and selectable resistor R sense connected as shown. R sense is preferably adjusted during manufacture. Additional control is provided for QRS sensitivity at line 36c, since the gain is delectable for this input.

Figure 3D:
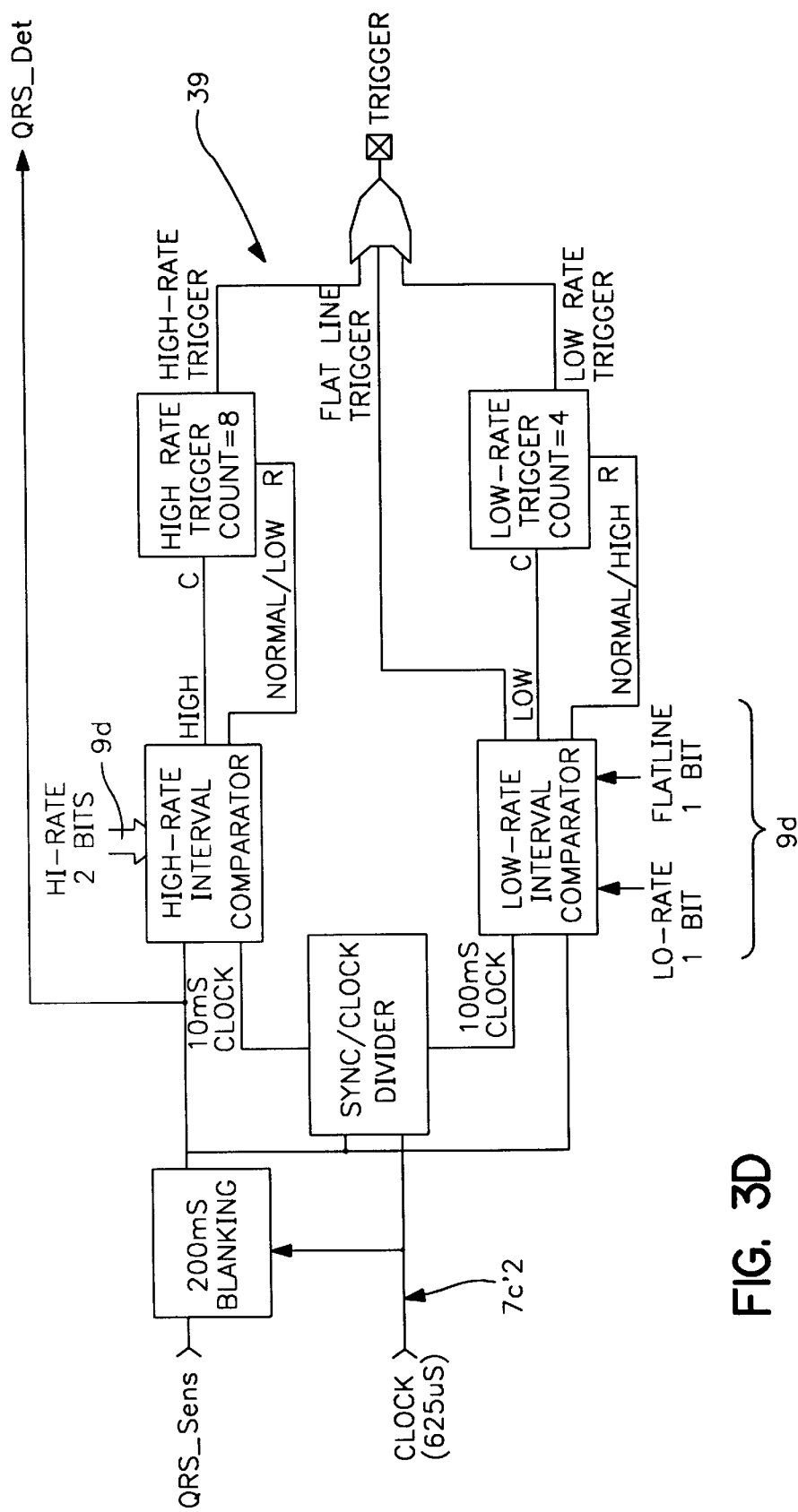

A simple arrhythmia detection circuit 39 is included with this preferred embodiment, and illustrated in FIG. 3D. The output from circuit 36 is monitored at a 200 millisecond blanking interval circuit, controlled by a clock input 7i2. In the preferred embodiment, a high rate can be selected amongst 4, with two selection bits dedicated to do so at input 9d and the low and flatline trigger rates each have one bit to turn them on or off provided by inputs 9d. These inputs designated 9d preferably come from a register that holds the gain the mode and the rate settings, illustrated as register 9 in FIG. 3. Such features may be programmable through communication with the implanted device by an external device. Preferred timing for the high rate triggers is 140, 162 and 182 beats per minute, requiring 8 consecutive beats at such a rate to initiate the trigger. Additionally the trigger may be programmed off. The low rate counter/comparitor may be programmable to detect low rates of 40 or 30 bpm, requiring 4 consecutive low rate intervals to trigger. Additionally a flat-line trigger can be set to occur after 3 or 4 and one half seconds of no QRS detection.

For embodiments that include more sensors and/or electronics, additional sensors could be added to benefit the patient. One particularly useful would be an activity sensor based on a single or multi-axis accelerometer, which indicates the level of patient activity and his orientation. By checking for output that indicates the occurrence of a VVS (Vaso Vagal Syncope) episode, (for example, the patient falling from an episode) such an addition offers an improved trigger for events that might otherwise be missed by an arrhythmia detector set up like in FIG. 3D. Such a sensor trigger could replace the circuitry of 3D.

Additional circuits may be provided to support additional functions if desired, however in order to reduce size and power consumption and extend the life of the device and reduce the intrusion into the body of the wearer, auxiliary circuits should be kept to a minimum. Such additional circuits could support temperature sensing, oxygen sensing, pressure sensing, respiration sensing, and any other kind of sensing that can be demonstrated to have been known for implanted devices. They may each have their own auto triggers based on sensor output, or depend on manual triggers. Additionally, activity sensing or positional sensing devices can provide additional input for recordation and or autotriggerring functions. As new sensors become available they may also be incorporated into these designs.

In considering size, the maximum dimension of the device need be only the minimum required dimension for good signal to be obtained from the two electrode areas. In our studies we have found useable signal for ECG monitoring at a distance of about ½ inch (1 cm). The best minimum electrode distance for current electronics at reasonable prices appears to be from ¾ inches to 2 inches.

ECG recording functionality for preferred embodiments

The most important function of the simple versions of this invention is the long term ECG monitoring of the subcutaneous (or intramuscular)ECG. The device continuously records and monitors the subcutaneous ECG in an endless loop of memory. In its primary mode the device is triggered to save/retain in memory the last X minutes or seconds of ECG data by the patient subsequent to feeling symptoms of interest (e.g. syncope, palpitations, etc.).

In the preferred embodiment with 128K of memory the device can store 42 or 21 minutes of ECG, which can be reset after offloading by telemetry to an external device for analysis and display. In one form there are four modes settable for patient trigger only and in another form there are autotriggers. In the patient only(also called "manual")trigger modes, the patient can capture either one or three events between offloadings at either no compression or at a compression ratio of 1:2 or some other device supported ratio. When setting the mode of the implant, the physician or attendant can decide whether to record data in a compressed mode or not in the preferred embodiment. If greater detail of the triggered ECG is required than can be developed from compressed data storage, the physician should select non-compressed recording, thereby limiting the time available to record. In some embodiments sample rate may be modified as well, but this is not preferred.

Compression is preferably done using a known compression algorithm implemented in hardware. Many types are known and software compression could be used if desired too. An excellent and easy to implement example is found in the article Arrhythmia Detection Program for an Ambulatory ECG Monitor by Mueller, copyright 1978, ISA, ISBN 876645, attached to this document as Appendix A. Using this algorithm in one embodiment we have used a pre-trigger time of record of a maximum of 2400 seconds and a maximum post trigger record of 120 seconds, and at the higher sampled or less compressed rate of 1200/60 for a single event and 360/60 seconds for three events. These time values are obviously only examples and the reader can set whatever time he or his physician feels is appropriate within the ambit of this invention. After such a record is made the device memory locations are full and will be overwritten by the next triggered event since in the preferred embodiment the memory is maintained in a continuous loop.

Additional modes include those with pure autotriggering, which can mirror the patient triggered only modes if desired. It should be considered that with autotriggered events, the determination by the device of an event worth recording and the subsequent activation of the trigger by the device itself will be faster than the patient finding his device for activation or otherwise activating the device, so the pre trigger time record can be smaller. In one preferred embodiment the memory is segmented to allow for 14 autotriggers and 3 manual triggers. Further detail regarding modes is described with reference to FIGS. 11 and 12.

The patient activated triggering of a preserved form of the recorded ECG signal can be carried out by using a small handheld external device which may be of any number of different forms. A first way is through a handheld battery-powered device which uses a coded radio-frequency telemetered signal through the skin to the device, on the press of a button. A simpler device a small handheld used to close a magnetic switch within the implanted device to trigger it by holding the magnet close or patting the area of the body that has the implant a set number of times with the magnet. Other methods for triggering ECG data retention in memory (each of which has it's own advantages for implementation) are to use physical tapping or slapping of the finger or hand on the skin over the device in a particular cadence and/or number of taps (advantage is that no triggering device is needed. With such methods the disadvantage is that the patient needs to memorize the triggering sequence. Matched voice activation with a known command is possible but the complexity at this time of discerning voice commands precludes such activation for the present time, but could be in future devices using this invention. Another approach is light activation through the skin using a light source and receiver, auditory/sonic activation using a handheld auditory/sonic source held over the skin with a microphone receiver in the device. All these methods are patient activated and require patient compliance or cooperation, a feature this device was designed to avoid. Accordingly in conjunction with one of these patient triggers or alone, an automatic activation or trigger for holding a chunk of memory should be included. This could be activated by automatic recognition of an arrhythmia, a heartbeat too fast or too slow, or for any other condition the device may be set up to find.

If a patient trigger is used it is advantageous provide feedback to the patient regarding whether the attempt to trigger long term storage of the event was successful. To accomplish this the implant should telemeter out a signal that indicates it has recognized a valid trigger. (This of course requires additional circuitry and usage of the limited available power supply.) The external triggering device then notifies the patient via the triggering device or through some known alarm mechanism whether they have or have not properly triggered the implanted device. This notification can be one of any combination of a number of feedback methods including: one or two visual sources such LED's, an auditory source such as a beeping speaker in one or two tones, or a tactile source such as a vibration. See also U.S. Pat. No. 5,518,001 for other potential trigger-indicator ideas for a hand-held patient activated trigger device.

Features and Construction of the preferred embodiment implantable devices

Figure 11:
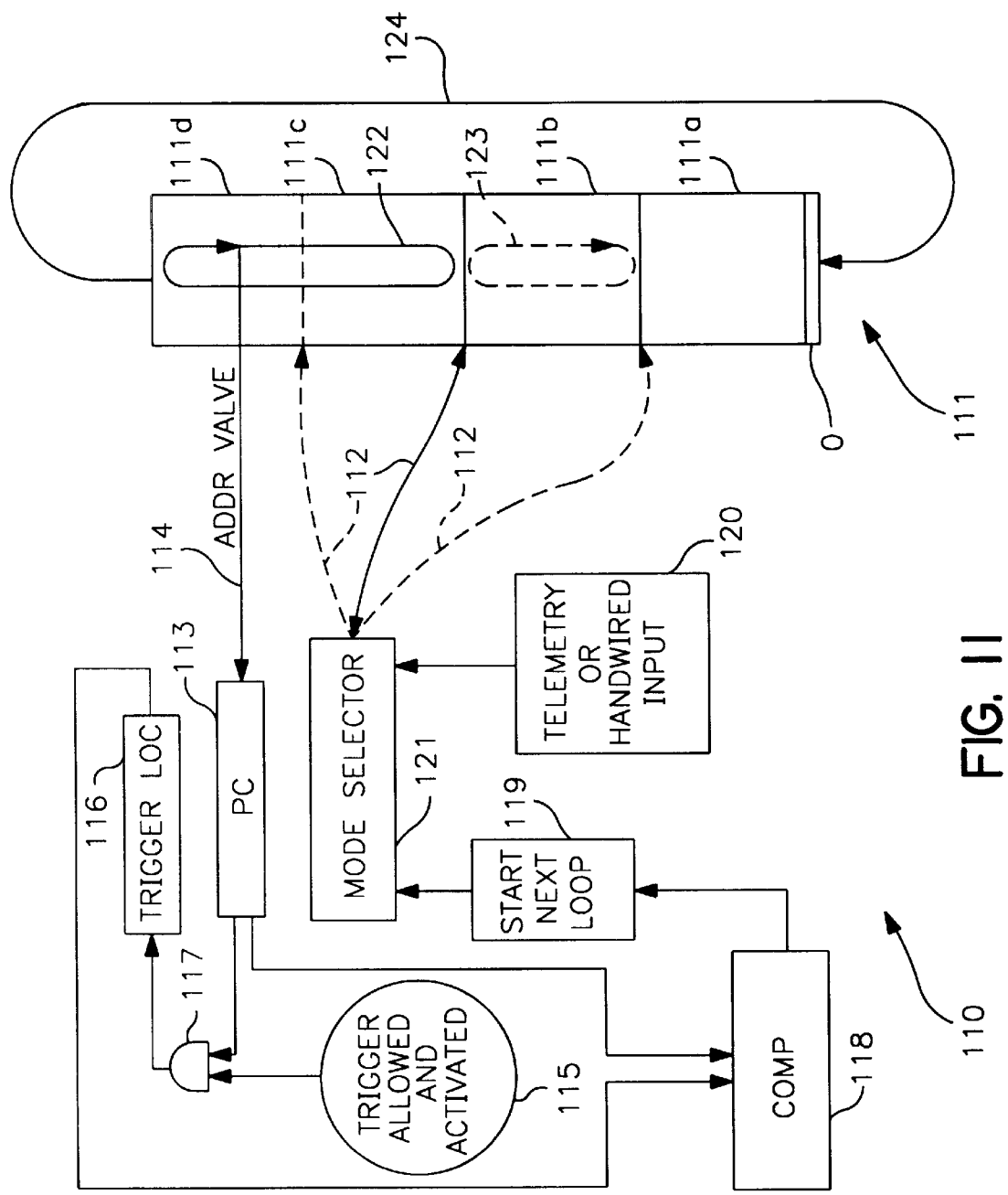
FIG. 11 is a block diagram of the looping memory and its control circuitry in accord with a preferred embodiment of the invention.

Referring now to FIG. 11 in which a block diagram of a functional model 110 of the controller and memory 111 of a preferred embodiment device is illustrated. The memory is generally organized as a continuous loop of, preferably, 8 bit addresses starting at address 0 and looping back around to address 0 through line 124. By telemetry or hard-wired input during manufacture 120, a mode selector 121 is set so as to divide the memory 111 into working segments 111a–d. The address of the start of each of these segments is indicated with lines 112.

Since this device is used for recording physiologic data, after the data is compressed, converted, formatted and is in appropriate digital form, it is continually recorded in the memory 111. The address value at the tip of arrow 122 in the combined memory space 111d, 111c is monitored by a program counter register 113.

The size of each memory segment set in a given mode limits the amount of data available for each triggered event. In the preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7, incorporated herein by reference in its entirety.

To use a single program counter the actual trigger address minus the time (in memory location storage events) required to have already stored the amount of data needed for pre event analysis for that trigger is stored as a value in the trigger location register 116 of FIG. 11. If a larger time for pre trigger recording is required by a trigger occurring during an already triggered event,(say, a manual trigger follows the occurrence of an auto trigger), the value in the trigger register can be decremented, thus yielding a larger pre trigger time period in the allocated memory segment for this event. A priority system for whether to extend the pre trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto triggered one because upon recovering from an event the patient has enough time to recover, get their wits about them, and find the triggering device. Manual triggering may therefore be set to record in double or multiple sized segments. FIG. 11's segments 111c and d are joined by looping arrow 122 to give effect to this concept.

Because the memory size is preferably quite limited a time record or first-in-first-out pool record should be kept on order that the newest triggers record only over the oldest events segments. An additional preferred feature allows for a mode that prevents recording over any triggered event segment. This is preferably implemented by a counter which fills for each segment used and has storage for the set number of looping segments. When it is full recording of new events stops.

When a trigger is activated and under the control program of the device is allowed, a signal 115 is permitted by some control gate 117 to allow the program counter address to be loaded into a trigger location address register 116. After loading, each subsequent clock cycle or set of clock cycles depending on the configuration of the device will load the trigger location from 116 into a comparator 118 to compare this location with the program counter address stored in register 113. When comparator 118 finds that they match, an appropriate output is generated to start the next loop via control circuit 119. This control circuit 119 will cause the mode selector to point to the next available loop location effectively placing that into the program counter 113.

Figure 12:
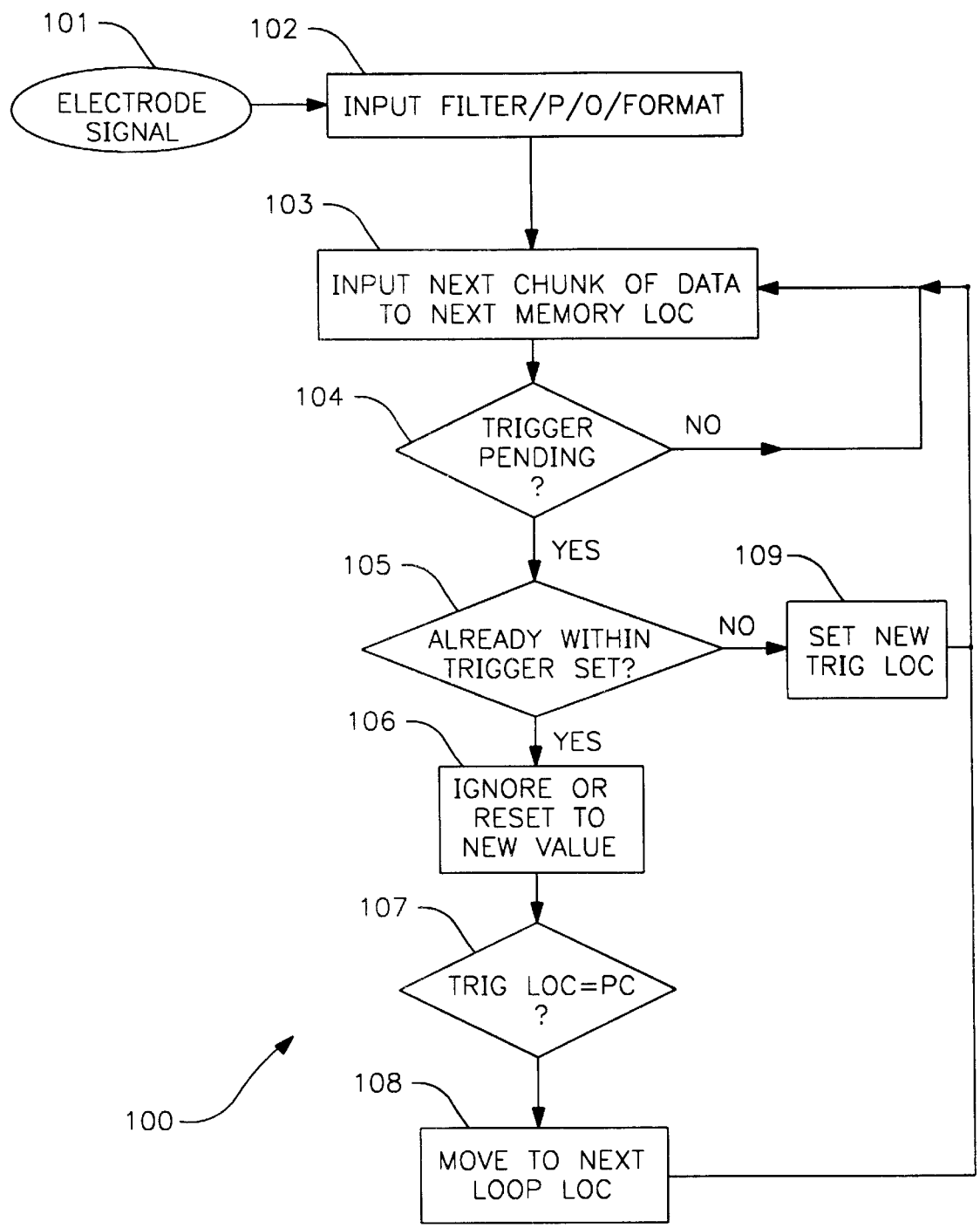
FIG. 12 is a flow chart of the functioning of the recordation of triggered events in a preferred embodiment of the invention.

The diagrammatic algorithm 100 to indicate the flow of this information is found in the illustration of FIG. 12 in which an electrode signal 101 is input filtered, converted from analog input to digital values, compressed and formatted if desired in step 102 so as to be in appropriate form to store in a memory location designated by a program counter pointer.

This data word's form could be containing a value representing input signal compressed at various available ratios, and may be mixed with other information like data provided by another sensor or clock data. The data stored will of course carry information related to the signal taken at the sampling rate. Thus lower sampling rates to save power will adversely affect the usefulness or detail of the data. Whatever its preferred form, each data point stored as a word is referred to as a chunk.

Output form step 102 provides the next chunk of data to the next memory location in step 103.

Device checks to see if there is any trigger pending after storing each chunk of data in step 104. If not, the next chunk of data is stored. If there is, the device preferably checks to see if there is another trigger already set and if so either ignores it or resets the value of the reserved looping memory area (like areas 111a–d in FIG. 11) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

It should be recognized that any of the inventive concepts taught herein may be applied to implantable devices to supplement their other functions, such as a supplemental recording system for a pacemaker, implantable drug pump, et cetera. Further, known enhancements to telemetric communication can be used to automatically activate offloading of data to a device located in the patient's home. Such a device could send its received communications to the attending care giver/physician's office at some convenient time, telephonically or otherwise so as to enable close compliance with prescribed follow-up of patient conditions. This invention is not understood to be limited in scope except by the following claims.

What is claimed is:

1. A minimally invasive implant for implantation beneath a skin and into a living body comprising;

a shell housing means having an inside and an outside, said outside forming a shape and having electrodes for sensing a physiologic parameter of said body, said electrodes located on said outside such that a substantially fixed spacing is maintained between said electrodes on said outside's shape, said electrodes being for electrical connection with the body and wherein said housing shape has a longitudinal dimension exceeding a transverse dimension, said transverse dimension being of a size suitable for insertion into said body with minimal opening requirements to the skin of said body, said minimal opening size being substantially no greater than ½ inch in maximum diameter, said inside having a power source and electronic circuitry powered thereby comprising at least an input means for sensing an electrical signal due to a physiologic parameter of said body connected to at least one of said electrodes, a memory means connected to accept output from said means for sensing, said memory means triggerable to use segments of said memory means by a trigger means and to store said output, as digital data representative of said physiologic parameter, and telemetry means connected to transmit data from said memory means upon activation of said telemetry means by a receiver means outside said body.

2. An implant as set forth in claim 1 wherein said outside shape has exactly two electrode areas located substantially at opposite ends of said longitudinal dimension.

3. An implant as set forth in claim 2 wherein said input means is a differential amplifier connected between said two electrode areas.

4. An implant as set forth in claim 1 wherein said memory is organized into a continuous loop such that each new datum regarding said physiologic parameter is stored in a subsequent memory location until said memory is full wherein the first location is overwritten and wherein a memory control means marks off segments of said memory such that triggered segments are not overwritten but skipped.

5. An implant as set forth in claim 1 wherein said memory is organized into a set of segments controlled by a mode control means for indicating location addresses of each segment and wherein each segment is organized into a continuous loop such that each new chunk of data regarding said physiologic parameter is stored in a subsequent memory location in a first segment loop until a trigger occurs indicating that an event should be stored, whereupon the trigger location is recorded and compared with a program counter which is updated by one memory chunk location after each new chunk is written, such that when said program counter value compares positively to said trigger location value, said segment loop memory is full whereupon the address of the next available segment is loaded into the program counter and the next chunk of data is stored at that new program counter location.

6. An implantable device as set forth in claim 5 wherein a counter means counts the number of segments holding recorded event data due to triggering events.

7. An implant as set forth in claim 1 wherein said electronic circuitry further comprises a memory controller means for storing data and wherein said memory controller means further comprises a data compression algorithm for directing the accumulation of said data into said memory means in accord therewith.

8. An implant as set forth in claim 7 wherein said memory controller means stores data in accord with a turning point data compression algorithm implemented in hardware.

9. An implant as set forth in claim 1 having an automatic trigger means comprising means for determining if a series of signals representing QRS complexes represents a heart rate that exceeds or falls below a predetermined range of rates.

10. An implant as et forth in claim 9 wherein said autotrigger means is enhanced by an additional sensor means in the device that determines position and movement, such that indications of VVS, are triggered based on output from said sensor means.

11. An implant as set forth in claim 9 wherein said device comprises communication circuit means responsive to patient signals that activate a trigger responsive to patient input.

12. An implant as set forth in claim 9 wherein said autotrigger means is enhanced by an additional sensor means in the device that determines position and movement, such that indications of VVS and other conditions leading to a loss of consciousness are triggered based on output from said position and movement sensor means.

13. An implant as set forth in claim 1 having an automatic trigger means comprising means for determining if a series of signals representing QRS complexes represents a heart rate that exceeds or falls below a predetermined range of rates, and additionally having a patient activatable manual trigger means.

14. An implant as set forth in claim 13 wherein when the trigger is manual, a temporal size of the memory available to be reserved for a recorded event is larger than the temporal memory size available to an automatically triggered event.

15. An implant as set forth in claim 1 wherein the exterior of the device has at least 3 electrodes wherein one is located on an appendage off a main body.

16. An implant as set forth in claim 1 provided with a suture securing means.

17. A device for recording physiologic events for implant into a body, said device being encapsulated in a hermetically sealed housing, having a longitudinal dimension substantially greater than a transverse dimension and wherein a transverse cross-section of the device is substantially elliptical or otherwise substantially flat wherein a substantially flat surface resulting from said substantially elliptical or otherwise flat cross section provides resistance to turning while implanted and having two electrodes substantially separated from each other along the longitudinal dimension, and having a memory for said recording.

18. A device as set forth in claim 17 provided with a suture securing means.

19. A device as set forth in claim 17 wherein said device has a shape adapted to be injectable with a trocar-like device, so as to be shaped for slidable mechanical urging against an inner surface of such a trocar-like device.

20. A device as set forth in claim 19 wherein said device additionally has inherent surface characteristics adapted to avoid movement once insertion is complete.

21. An implant as set forth in any of claims 1–6 or 7–20, wherein a sensor provides temperature data for recording in said memory.

22. An implant for recording physiologic events in a body, having a hermetically sealed housing with a longitudinal dimension substantially greater than a transverse dimension and wherein a transverse cross-section of the device is substantially elliptical or otherwise substantially flat wherein a substantially flat surface resulting from said substantially elliptical or otherwise flat cross section provides resistance to turning while implanted, and having sensors within said housing for generating data regarding physiologic conditions within a patient's body and circuit means for storing representations of said conditions in a memory means also within said housing.

* * * * *